US005959193A

United States Patent [19]

Rubitschung et al.

[11] Patent Number: 5,959,193

[45] Date of Patent: Sep. 28, 1999

[54] EXPLOSION PROTECTION APPARATUS WITH ELECTRICAL INITIATION

[75] Inventors: Christoph Rubitschung, Lampenberg, Switzerland; Denis Bubendorf, Ranspach-le-bas, France

[73] Assignee: Rubitec AG, Holstein, Switzerland

[21] Appl. No.: 08/909,840

[22] Filed: Aug. 12, 1997

[30] Foreign Application Priority Data

| | | | |
|---|---|---|---|
| Aug. 13, 1996 | [CH] | Switzerland | 1992/96 |
| Jun. 4, 1997 | [EP] | European Pat. Off. | 97810343 |

[51] Int. Cl.$^6$ .......... G01N 33/22

[52] U.S. Cl. .......... 73/35.17; 49/31

[58] Field of Search .......... 73/35.14, 35.17, 73/31.05; 109/15; 241/31; 49/31, 68

[56] References Cited

U.S. PATENT DOCUMENTS

| | | | |
|---|---|---|---|
| 1,868,708 | 7/1932 | Hunt | 137/75 |
| 2,917,927 | 12/1959 | Clark | 73/35.17 |
| 3,214,156 | 10/1965 | Klose et al. . | |
| 3,268,107 | 8/1966 | Sperling | 73/35.17 |
| 3,831,318 | 8/1974 | Richmond | 49/31 |
| 4,083,226 | 4/1978 | Eckstein et al. | 73/31.05 |

FOREIGN PATENT DOCUMENTS

| | | |
|---|---|---|
| 2234501 | 1/1975 | France . |
| 4316584 | 8/1994 | Germany . |
| 440894 | 1/1968 | Switzerland . |
| 685134 | 3/1995 | Switzerland . |

*Primary Examiner*—Hezron Williams
*Assistant Examiner*—Helen C. Kwok
*Attorney, Agent, or Firm*—Selitto & Associates

[57] ABSTRACT

An explosion protection apparatus for installation in potentially explosive industrial installations for the purpose of automatically preventing a pressure wave and/or flame breaking through from a potentially explosive installation part to adjacent installation parts, has a sensor for explosion identification, which can be arranged in the potentially explosive installation part or can be connected to it. The sensor is electrically connected to an initiation device (1) which, in its basic state, holds a closing device (3) in its open position via an interlocking device (2) and with the aid of an active magnetic field of an electromagnet (5), and can be operated by sensor signals. The closing device (3) is prestressed such that, after operation of the initiation device (1), it is moved to its closed position. It can be arranged between the installation parts to be protected and the potentially explosive installation part.

17 Claims, 3 Drawing Sheets

EXPLOSION PROTECTION APPARATUS WITH ELECTRICAL INITIATION

FIELD OF THE INVENTION

The present invention relates to an explosion protection apparatus for installation in potentially explosive industrial installations.

BACKGROUND OF THE INVENTION

In some processes which are used in process gas technology, there is risk of gas explosions occurring. Measures therefore have to be taken in order physically to limit explosions in the industrial installations. Explosion protection apparatuses, such as fast-closing valves or slide valves, are used for this purpose, these being intended to prevent pressure waves and flames breaking through from a potentially explosive installation part into adjacent installation parts.

If an explosion occurs, it must first be identified. A closing command must then be issued and the closing process initiated and completed before the pressure wave and flame arrive at the relevant point.

Valves and slide valves are known having a compressed-air cylinder as drive and a compressed-gas reservoir having more than 10 bar overpressure in order to provide the closing energy. An explosive capsule valve and a compressed-air hose are arranged between the compressed-gas reservoir and the compressed-air cylinder. An incipient explosion is identified by a pressure sensor or an infrared sensor, and the explosive capsule valve is detonated electrically. This valve opens so that stored gas can flow from the compressed-gas reservoir via the compressed-air hose into the compressed-air cylinder, and closes the valve or the slide valve.

However, such valves and slide valves have the disadvantage that a relatively long time passes from the opening of the explosive capsule valve until the compressed-air piston is set in motion. In addition, the explosive capsule must be replaced whenever the compressed-gas reservoir is initiated. It is thus impossible to test these elements realistically.

Swiss Patent No. 685 134 discloses an explosion protection apparatus of the type mentioned initially, in which the compressed-air piston is a differential piston with a peripheral annular surface and an inner surface which is arranged concentrically with respect to said annular surface, whereas the peripheral annular surface and the inner surface can be acted on by a pressure generator and a compressed-gas reservoir. The pressure generator, which is initiated by the sensor, gives the differential piston a high initial acceleration which, once the inner surface has lifted off its contact surface, is further reinforced by the pressure from the pressure generator and the compressed-gas reservoir acting over the entire area of the differential piston.

This explosion apparatus admittedly allows short closing times to be achieved; however, it still has the disadvantage that the pressure generator is either a pyrotechnic element having a powder filling which can be detonated electrically or is a compressed-gas cartridge which releases the compressed gas by means of an explosive capsule which can be detonated electrically. Once again, it is thus impossible to test the pressure generator realistically.

Pyrotechnic detonators also have the major disadvantage that they are subject to weapon laws in some countries, which at least makes commercialisation more difficult. In addition, they require the wire from the sensor to the detonator to be protected against fracturing, in order to ensure reliable explosion protection.

DE-C1-43 16 584 discloses an apparatus for shutting off supply lines which are connected to building connections and are acted on by gases, which apparatus has a closing device which is arranged in a housing and is held in its open position by an initiation device in the basic state. The closing device is prestressed by means of a compression spring such that it is moved to its closed position once the initiation device has operated. The initiation device is operated by switching a solenoid valve, controlled by a control center, which is connected to the solenoid valve, as a function of signals which are obtained from gas detectors, smoke detectors, temperature sensors and/or a flow monitor.

In terms of the definition of its purpose, the shut-off apparatus is not an explosion protection apparatus and, in consequence, is also not aimed at achieving a closing time which is as short as possible in response to an explosion. In order to operate the initiation device, the solenoid valve must first build up a magnetic field, which takes at least about 50 ms. This is much too slow for an explosion protection apparatus.

SUMMARY OF THE INVENTION

With regard to the present disadvantages of the previously known apparatuses as described above, the invention is based on the following object. An explosion protection apparatus of the type mentioned initially is to be provided, by means of which short closing times can be achieved without using a pyrotechnic detonator. This object is achieved by the explosion protection apparatus according to the invention.

The essence of the invention is that, in the case of an explosion protection apparatus for installation in potentially explosive industrial installations for the purpose of automatically preventing a pressure wave and/or flame breaking through from a potentially explosive installation part to adjacent installation parts, an initiation device is prestressed in its basic state and comprises a magnet which has a magnetic field which is active in order to hold the initiation device in its basic state. The explosion protection apparatus comprises at least one closing device which can be arranged between the installation part to be protected and the potentially explosive installation part, is held in its open position by the initiation device in its basic state, and is prestressed such that, after operation of the initiation device, it is moved to its closed position. The initiation device is electrically connected to a sensor for explosion identification, which sensor can be arranged in the potentially explosive installation part or can be connected to said installation part, and can be operated by sensor signals.

Short closing times can be achieved, even without any pyrotechnic detonators, by the electrical transmission of the sensor signal to the initiation device, electromagnetic initiation of the closing movement and prestressing of the closing device. As a result of the fact that the initiation device is held prestressed in its basic state by the active magnetic field of the magnet and, for operation, it is only necessary to break down the already existing magnetic field without having to build up a magnetic field first, the closing times are also considerably shorter than in the case of initiation devices having solenoid valves.

The explosion protection apparatus according to the invention can be tested repeatedly, since no irreversible steps are carried out during the initiation of the closing movement.

In a preferred design variant, an electromagnet is used as the magnet, which holds the initiation device in its basic state when power is supplied, as a result of which the closing device is held in its open position. The electromagnet is supplied with power as long as the initiation device receives signals from the sensor which indicate that no explosion has yet occurred. If an explosion occurs, or the signal is not transmitted correctly between the sensor and the initiation device because of a defect in the wire, a closing movement is initiated.

This design variant has the advantage that it is not necessary to monitor the wire in order to ensure reliable explosion protection. However, wire monitoring can optionally be used in order to prevent spurious initiation operations.

The already mentioned magnet advantageously has arranged behind it at least one further magnet which increases the force for holding the initiation device in its basic state, power being supplied to the magnets in parallel. This makes it possible to prestress the initiation device more strongly and to reduce the initiation time further.

BRIEF DESCRIPTION OF THE DRAWINGS

The explosion protection apparatus according to the invention will be described in more detail in the following text using exemplary embodiments and with reference to the attached drawings, in which.

DETAILED DESCRIPTION OF THE INVENTION

FIG. 1

Figure 1:
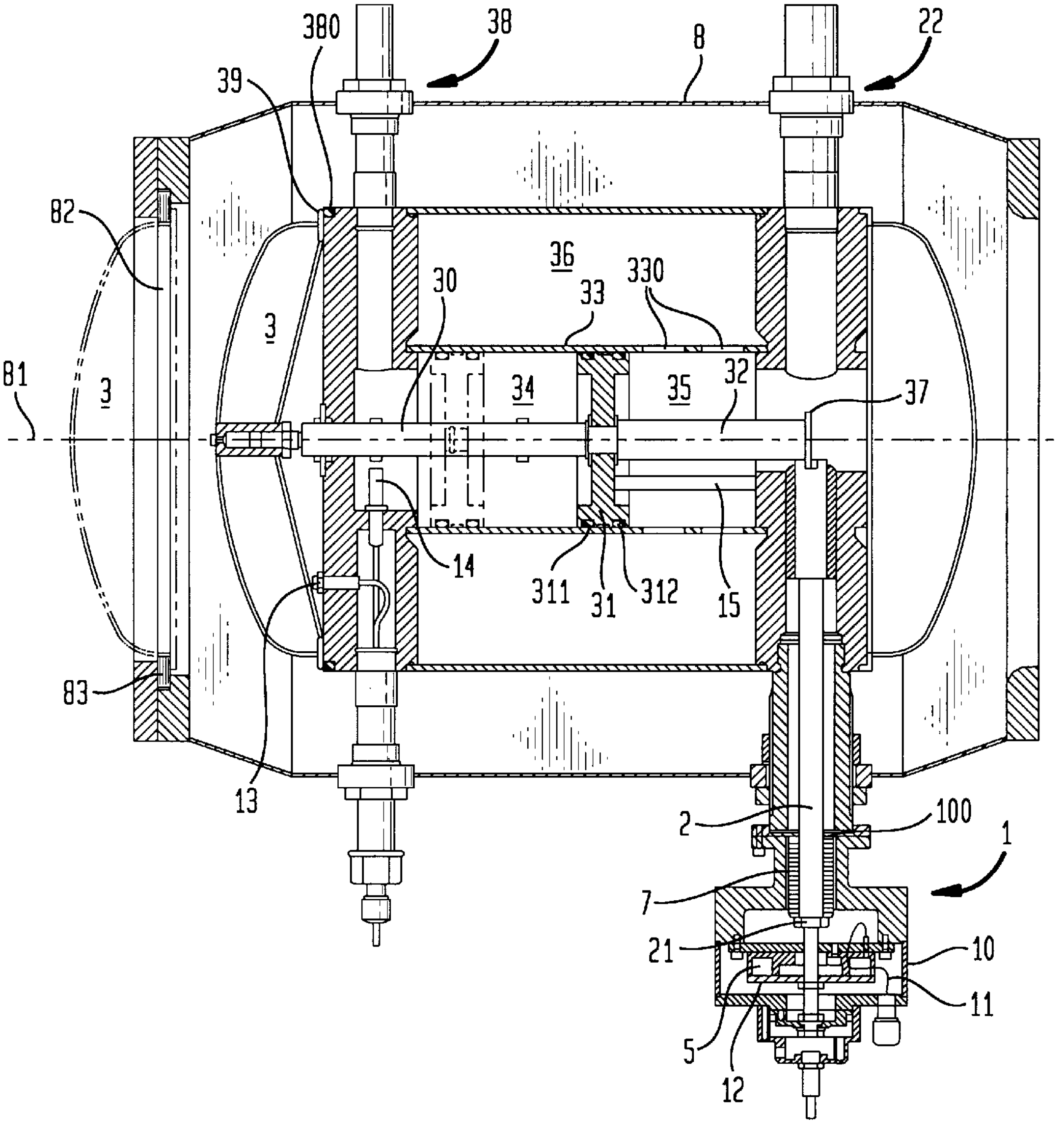
FIG. 1 shows a section view of an explosion protection apparatus which is fitted to a tube and has an axial valve which closes on one side.
Figure 2:
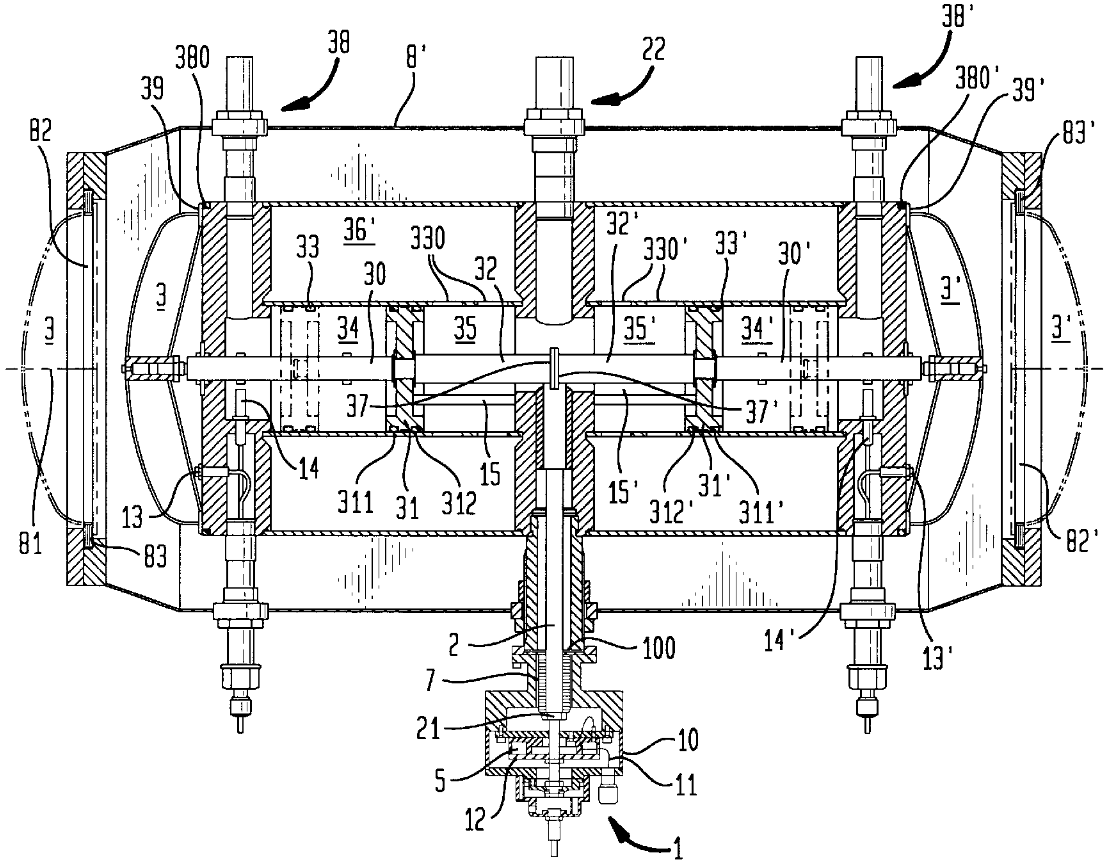
FIG. 2 shows a section view of an explosion protection apparatus which is fitted to a tube and has an axial valve which closes on two sides.

The explosion protection apparatus, the majority of which is fitted to a tube 8, has an initiation device 1 with a housing 10 in which an annular electromagnet 5 is arranged. A wire 11 is used for supplying power to the electromagnet 5, which power supply is controlled by a sensor (which is not illustrated) for explosion identification of a known type, in particular a pressure or infrared sensor, which is arranged in an adjacent potentially explosive installation part, or is connected to it.

An interlocking device 2 extends through the center of the annular electromagnet 5, at right angles to the center axis 81 of the tube 8 and virtually as far as it. The interlocking device 2 is mounted on one side in the initiation device 1 and on the other side in a support device 22, which is at the same time used as an interlocking housing. When power is supplied to the electromagnet 5, the interlocking device 2 is moved by the electromagnet 5 in the direction of the tube center axis 81, as a result of electromagnetic attraction of a metal plate 12 which is firmly connected to the interlocking device 2.

Arranged between a housing wall 100 of the initiation device 1, which housing wall 100 faces the tube 8, and a spring support 21 which is fitted to the interlocking device 2 there is a compressed spring 7, in this case a spiral spring, which has the tendency to force the interlocking device 2 away from the tube center axis 81, and thus prestresses the interlocking device 2.

The end of the interlocking device 2 facing the tube center axis 81 is designed in a U-shape for holding a holding element 37, with the opening towards the tube center axis 81.

A cylinder 33, in which a piston 31 is mounted such that it can move, is fitted in a fixed position between the support device 22 and a support device 38. Annular seals 311, 312, which ensure sealing towards the inner cylinder wall, are arranged on the periphery of the piston 31. The cylinder 33 is split by the piston 31 into a first chamber 34, which is subject to a relatively low pressure $p_1$, and a second chamber 35, which is subject to a pressure $p_2$ which is greater than that in the first chamber 34. The overpressure in the second chamber 35, which is, for example, about 6 bar, would move the piston 31 towards the support device 38, if it were not hold back. The piston 31 is thus prestressed.

A compressed-gas reservoir 36, which is arranged in a toroidal shape around the cylinder 33 and is connected via cylinder openings 330 to the second chamber 35, ensures that there is sufficient overpressure in the second chamber 35 while the piston is moving towards the support device 38, this movement being linked with an increase in the volume of the second chamber 35.

A domed closing device 3 is connected via a first piston rod 30 to one side of the piston 31, so that it is moved during movement of the piston. The closing device 3 is provided with a sealing flange 39 which, in the closed position, comes to rest against an annular seal 83 which bounds the tube opening 82, thus ensuring sealed closure of the tube opening 82. An annular seal 380 which is arranged on the support device 38 ensures that, in the operating position in which the sealing flange 39 rests against the support device 38, no dirt can enter the space between the closing device 3 and the support device 38.

In addition, two motion sensors 13, 14, for example inductive position sensors, are fitted to the support device 38 and are used to monitor the motion of the closing device 3 and of the first piston rod 30.

The opposite side of the piston has extending from it in the direction of the support device 22 a second piston rod 32, at whose end facing away from the piston 31 the holding element 37 is arranged which, in the interlocked position, engages in the U-shaped end of the interlocking device 2. In this position, the tube opening 82 is open. A rod 15, which is arranged between the piston 31 and the support device 22 and is used as a stop for the piston 31, ensures that the holding element 37 is positioned accurately in the interlocked position. If need be, the rod 15 can be dispensed with, since accurate positioning of the holding element 37 can also be achieved by using the support device 38 as a stop for the closing device 3.

The described explosion protection apparatus functions as follows:

In the operating position, which is illustrated by solid lines, the electromagnet 5 is supplied with power as long as the initiation device 1 receives signals from the sensor which indicate that no explosion has yet been identified. The electromagnet 5 forces the interlocking device 2 towards the tube center axis 81. The interlocking device 2, in whose U-shaped end the holding element 37 engages, holds the closing device 3 in its open position, via the second piston rod 32, the piston 31 and the first piston rod 30. Any process gas can flow through the tube opening 82 and the tube 8.

If the sensor identifies an explosion or if the signal transmission between the sensor and the initiation device is defective, the power supply to the electromagnet 5 is interrupted, the interlocking device 2 is moved away from the tube center axis 81 by the spring 7, and the U-shaped end of the interlocking device 2 releases the holding element 37. As a result of the overpressure in the second chamber 35 which is maintained with the aid of a compressed-gas reservoir 36, the piston 31 is moved towards the support device 38, and the closing device 3 is thus moved towards the tube opening 82, until it reaches its closed position, that is to say the sealing flange 39 is resting against the annular seal 83 to provide a seal. The tube opening 82 is then closed, providing a seal, and preventing the pressure wave and flame of the explosion from breaking through. The closed position of the closing device 3 and of the piston 31 is illustrated by dashed lines in FIG. 1.

The following definition applies to all the rest of the description. Where a figure includes reference numbers for the sake of clarity in the drawing, but these are not explained in the directly associated description text, then reference should be made to where they are mentioned in preceding figure descriptions.

FIG. 2

Arranged in a tube 8', there are two axial valves which close in opposite directions and are of identical construction to the axial valve illustrated in FIG. 1. The reference numbers 3', 13'–15', 30'–35', 37'–39', 82', 83', 311', 312', 330' and 380' designate elements corresponding to the elements 3, 13–15, 30–35, 37–39, 82, 83, 311, 312, 330 and 380. A compressed-gas reservoir 36' is arranged in a toroidal shape both around the cylinder 33 and around the cylinder 33'. The closing movements are initiated in the same way as in the case of the first design variant.

This second design variant has the advantage that closing movements take place in two opposite directions. This ensures that one closing movement is always assisted by the pressure wave of the explosion.

FIG. 3

In this design variant, the explosion protection apparatus has a slide valve instead of an axial valve. The closing device 4 is once again held in its open position by an interlocking device 2 with a U-shaped end, via a first piston rod 40, a piston 41 with annular seals 411, 412 and a second piston rod 42 with a holding element 47. The cylinder 43, which is associated with the piston 41, is split by said piston 41 into a first chamber 44 and a second chamber 45 and is arranged between the support device 22 and a support device 48. The initiation device 1 and the method of operation of the explosion protection apparatus are essentially the same as in the case of the two first design variants, except for the fact that, in this case, the closing device 4 is pushed from the side over a tube opening 802 of a tube 80, and the overpressure in the second chamber 45 is maintained by means of a compressed-gas reservoir (which is not illustrated) via a compressed-air duct 360.

FIG. 4

Figure 3:
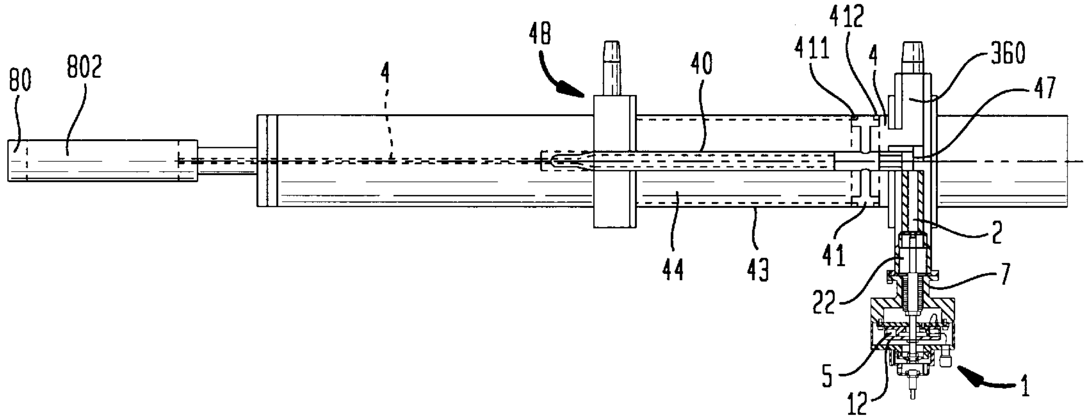
FIG. 3 shows a section view of an explosion protection apparatus which is arranged at the side of a tube, with a slide valve in the open position and an initiation device with an electromagnet.
Figure 4:
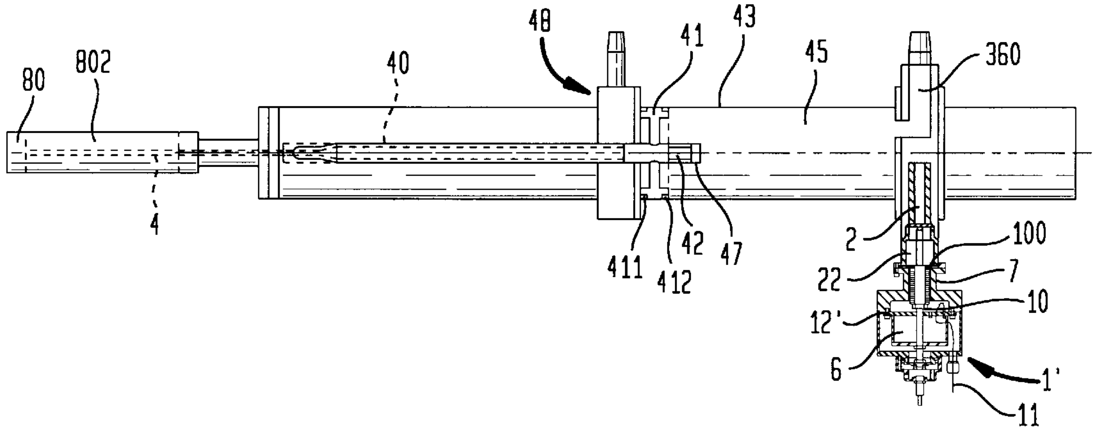
FIG. 4 shows a section view of an explosion protection apparatus which is arranged at the side of a tube, with a slide valve in the closed position and an initiation device with a permanent magnet.
Figure 5:
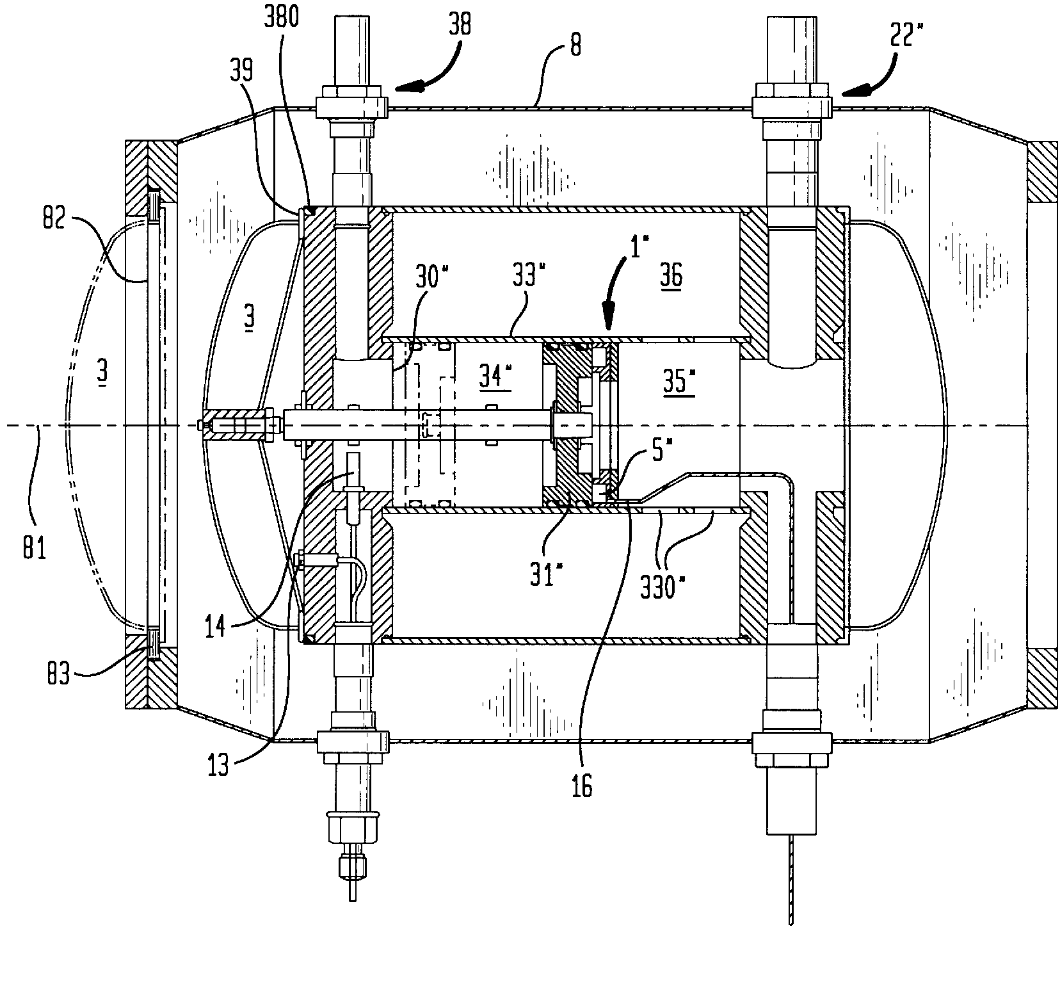
FIG. 5 shows a section view of an explosion protection apparatus which is fitted to a tube and has an axial valve which closes on one side and an alternative initiation device.

Except for the initiation device 1', this design variant corresponds to that illustrated in FIG. 3, the closing device 4 in this case being in the closed position.

Instead of an electromagnet 5, the initiation device 1' has a permanent magnet 6 which holds the interlocking device 2 in its interlocked position against the prestress produced by the spring 7 by means of electromagnetic repulsion of a metal plate 12' which is firmly connected to the interlocking device 2, until an explosion is signalled by the sensor. When an explosion is signalled, the permanent magnet 6 is compensated for by a supply of power, the interlocking device 2 being operated by the spring prestressing when said supply of power is applied.

FIG. 5

In this design variant, only one piston rod 30" is fitted to a piston 31" arranged in a cylinder 33", the interior of the cylinder 33" being split by the piston 31" into a first chamber 34", to which the piston rod 30" is assigned and which is subject to a relatively low pressure $p_1$, and a second chamber 35", which is subject to a pressure $p_2$ which is greater than that in the first chamber 34". An initiation device 1" is fitted in a fixed position in the second chamber 35" and, by means of an annular electromagnet 5", holds the closing device 3 in its open position, via the piston rod 30" and the piston 31", by electromagnetic attraction of the piston 31", for as long as power is supplied to the electromagnet 5". Power is supplied via an electrical cable 16 which is introduced into the cylinder 33" through the support device 22", and the power is controlled by the sensor signals, as in the design variants described above.

In the event of an interruption in the power supply, the electromagnet 5" loses its force of attraction, and the closing device 3 is moved to its closed position by the overpressure in the second chamber 35" in comparison with the first chamber 34". Once again, the compressed-gas reservoir 36, which is connected to the second chamber 35" via cylinder openings 330", ensures that there is sufficient overpressure in the second chamber 35" throughout the entire movement of the closing device 3.

Further design variations to the above described explosion protection apparatuses can be implemented. It should be mentioned specifically here that the prestressing of the interlocking device 2 can also take place in a manner other than that described. For example, the arrangement of an extended spring in the support device 22 would be conceivable, one end of the spring being connected to the support device 22, and the other end to the interlocking device 2.

We claim:

1. An explosion protection apparatus for use in a tube having a tube opening, said apparatus comprising:

sensing means for sensing an explosion in said tube and for generating a signal in response thereto;

closing means for closing said tube opening, said closing means being movable between a first position, in which said closing means is spaced from said tube opening, and a second position, in which said closing means is in sealing engagement with said tube opening;

magnetic means for generating a magnetic field sufficient to hold said closing means in said first position; and interrupting means for interrupting said magnetic field in response to the signal generated by said sensing means, whereby upon interruption of said magnetic field, said closing means moves from said first position to said second position.

2. An explosion protection apparatus according to claim 1, wherein said tube opening includes an annular seal, and wherein said closing means includes a domed closing device having a sealing flange which engages said annular seal, such that said domed closing device is in sealing engagement with said tube opening when said closing means is in said second position.

3. An explosion protection apparatus according to claim 1, wherein said magnetic means includes an electromagnet and wherein said interrupting means terminates power supplied to said electromagnet.

4. An explosion protection apparatus according to claim 1, wherein said magnetic means includes a permanent magnet and wherein said interrupting means supplies power to said permanent magnet.

5. An explosion protection apparatus according to claims 3 or 4, wherein said sensing means includes a pressure sensor.

6. An explosion protection apparatus according to claims 3 or 4, wherein said sensing means includes an infrared sensor.

7. An explosion protection apparatus according to claim 1, wherein said magnetic means includes at least two magnets, thereby increasing the strength of said magnetic field.

8. An explosion protection apparatus according to claim 1, further comprising a wire connecting said sensing means and said interrupting means; and monitoring means for monitoring said wire, such that when said monitoring means detects a defect in said wire, said monitoring means generates a signal in response thereto, said interrupting means receiving the signal generated by said monitoring means and interrupting said magnetic field, thereby allowing said closing means to move from said first position to said second position.

9. An explosion protection apparatus according to claim 1, further comprising holding means for releasably holding said closing means in said first position, said holding means including an interlocking device movable between an extended position, in which said interlocking device is engaged with said closing means, thereby holding said closing means in its said first position, and a retracted position, in which said interlocking device is disengaged from said closing means, thereby allowing said closing means to move to its said second position; and a spring connected to said interlocking device, said spring being counteracted by said magnetic field such that upon interruption of said magnetic field, said spring moves said interlocking device from said extended position to said retracted position, thereby permitting said closing means to move from said first position to said second position.

10. An explosion protection apparatus according to claim 9, further comprising a fixed-position cylinder located in said tube, said cylinder having an interior;

a movable first piston rod located in said interior of said cylinder, said first piston rod having a first end and a second end, said first end of said first piston rod being connected to said closing means;

a movable piston located in said interior of said cylinder, said second end of said first piston rod being connected to said piston; and a movable second piston rod located in said interior of said cylinder, said second piston rod having a first end and a second end, said first end of said second piston rod being connected to said piston, said second end of said second piston rod being releasably held by said holding means.

11. An explosion protection apparatus according to claim 10, wherein said piston divides said interior of said cylinder into a first chamber and a second chamber, said first chamber housing said first piston rod and having a first pressure, said second chamber housing said second piston rod and having a second pressure which is greater than said first pressure, such that when said holding means releases said second piston rod, said second pressure moves said piston towards said first chamber, thereby moving said first piston rod and hence said closing means from said first position to said second position.

12. An explosion protection apparatus according to claim 1, further comprising holding means for releasably holding said closing means in said first position;

a fixed-position cylinder located in said tube, said cylinder having an interior;

a movable first piston rod located in said interior of said cylinder, said first piston rod having a first end and a second end, said first end of said first piston rod being connected to said closing means;

a movable piston located in said interior of said cylinder, said second end of said first piston rod being connected to said piston; and a movable second piston rod located in said interior of said cylinder, said second piston rod having a first end and a second end, said first end of said second piston rod being connected to said piston, said second end of said second piston rod being releasably held by said holding means.

13. An explosion protection apparatus according to claim 12, wherein said piston divides said interior of said cylinder into a first chamber and a second chamber, said first chamber housing said first piston rod and having a first pressure, said second chamber housing said second piston rod and having a second pressure which is greater than said first pressure, such that when said holding means releases said second piston rod, said second pressure moves said piston towards said first chamber, thereby moving said first piston rod and hence said closing means from said first position to said second position.

14. An explosion protection apparatus according to claims 11 or 13, wherein said second chamber is connected to a compressed gas reservoir having a third pressure which is equal to said second pressure, such that while said piston is moving towards said first chamber, gas from said compressed gas reservoir enters said second chamber, thereby ensuring that said second pressure in said second chamber is greater than said first pressure in said first chamber as said second chamber increases in volume due to the movement of said piston.

15. An explosion protection apparatus according to claim 1, wherein said closing means is part of an axial valve.

16. An explosion protection apparatus according to claim 1, wherein said closing means is part of a slide valve.

17. An explosion protection apparatus according to claim 1, wherein said tube includes another tube opening and wherein said apparatus includes another closing means for closing said another tube opening.

* * * * *